United States Patent
Wheeler et al.

(10) Patent No.: US 7,314,505 B1
(45) Date of Patent: Jan. 1, 2008

(54) STATIONARY PHASE DEPOSITION BASED ON ONIUM SALTS

(75) Inventors: David R. Wheeler, Albuquerque, NM (US); Patrick R. Lewis, Albuquerque, NM (US); Shawn M. Dirk, Albuquerque, NM (US); Daniel E. Trudell, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 275 days.

(21) Appl. No.: 11/156,975

(22) Filed: Jun. 20, 2005

(51) Int. Cl.
*B01D 53/02* (2006.01)

(52) U.S. Cl. ............... 95/83; 95/82; 96/101; 73/23.39; 210/635; 210/656; 210/198.2

(58) Field of Classification Search ............ 95/82, 95/83, 88; 96/101; 73/23.35, 23.39; 210/635, 210/656, 198.2, 502.1
See application file for complete search history.

(56) References Cited

U.S. PATENT DOCUMENTS

| | | | | |
|---|---|---|---|---|
| 4,043,905 | A * | 8/1977 | Novotny et al. | 210/198.2 |
| 4,199,330 | A * | 4/1980 | Nestrick et al. | 95/82 |
| 4,242,227 | A * | 12/1980 | Nestrick et al. | 502/402 |
| 4,276,061 | A * | 6/1981 | Nestrick et al. | 95/88 |
| 4,756,971 | A * | 7/1988 | Virtanen et al. | 428/405 |
| 4,757,023 | A * | 7/1988 | Trestianu et al. | 436/154 |
| 4,780,116 | A * | 10/1988 | Cheh et al. | 96/102 |
| 5,262,052 | A * | 11/1993 | Rossiter et al. | 210/635 |
| 5,431,821 | A * | 7/1995 | Olesik et al. | 210/635 |
| 5,637,135 | A * | 6/1997 | Ottenstein et al. | 96/101 |
| 6,068,684 | A | 5/2000 | Overton | |
| 2002/0056686 | A1 * | 5/2002 | Kyrlidis et al. | 210/656 |
| 2003/0042205 | A1 * | 3/2003 | Gaudet et al. | 210/656 |

OTHER PUBLICATIONS

C. Watanabe, "Features of Metal Capillary Columns," J. Microcolumn Separations, 12, 6, (2000) 345-350.
C. M. Matzke, "Microfabricated silicon gas chromatographic micro-channels: fabrication and performance," SPIE, Ro. 3511, Sep. 1998, 262-267.
Gordon Lambertus, "Design, Fabrication, and Evaluation of Microfabricated Columns for Gas Chromatography," Anal. Chem. (2004) 76, 2629-2637.
Jennifer A. Harnisch, "Chemical Modification of Carbonaceous Stationary Phases by Reduction of Diazonium Salts," Anal Chem. 2001, 73, 3954-3959.
Michael P. Stewart, "Direct Covalent Grafting of Conjugated Molecules onto Si, GaAs, and Pd Surfaces from Aryldiazonium Salts," J. Am. Chem. Soc., (2004), 126, 370-378.
Jean Pinson, "Attachment of organic layers to conductive or semiconductive surfaces by reduction of diazonium salts," Chem. Soc. Rev., (2005), 34, 429-439.
U.S. Appl. No. 11/065,894, filed Feb. 11, 2005, Dirk et al.

* cited by examiner

*Primary Examiner*—Duane Smith
*Assistant Examiner*—Robert A Clemente
(74) *Attorney, Agent, or Firm*—Kevin W. Bieg (57) ABSTRACT

Onium salt chemistry can be used to deposit very uniform thickness stationary phases on the wall of a gas chromatography column. In particular, the stationary phase can be bonded to non-silicon based columns, especially microfabricated metal columns. Non-silicon microfabricated columns may be manufactured and processed at a fraction of the cost of silicon-based columns. In addition, the method can be used to phase-coat conventional capillary columns or silicon-based microfabricated columns.

21 Claims, 6 Drawing Sheets

STATIONARY PHASE DEPOSITION BASED ON ONIUM SALTS

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to gas chromatography columns and, in particular, to an onium-based, stationary-phase-coated column and a method to coat the column with a stationary phase using onium salt chemistry.

BACKGROUND OF THE INVENTION

Gas chromatography (GC) relies upon the chemical equilibria of analytes between a mobile phase and a stationary phase in a GC column to bring about a temporal separation of the analytes in a gas mixture into a series of elution bands. An ideal gas chromatographic column has a high resolving power, high speed of operation, and high capacity. Most current methods of gas chromatography rely on an open capillary tube with a stationary phase coating the inner wall of the tube to generate chemical separations. These columns are typically made of high purity synthetic amorphous silicon dioxide (fused silica) or borosilicate glass capillary tubing. See R. L. Grob and E. F. Berry, *Modern Practice of Gas Chromatography*, 4$^{th}$ Ed., Wiley-Interscience (2004). However, recently there has been interest in metal capillary columns, because metal columns withstand elevated temperatures, endure buildup of substances with high boiling points, and have a large sample capacity. See Watanbe et al., "Features of Metal Capillary Columns", *J. Microcolumn Separations* 12(6), 345 (2000). As an alternative to the open capillary column, the column can be packed with a support that is coated with a stationary phase to achieve chemical separations. Regardless of the column type, to achieve good column performance requires a stationary phase that is selective of the analytes to be separated, has a high coating efficiency, is chemically stable, and has a wide operating temperature range.

Separations are the result of selective analyte-stationary-phase interactions and differences in the solubility of the analytes to be separated. Analyte-stationary-phase interactions include ionic, charge transfer, dipole-dipole, and hydrogen bonding. A stationary phase with like functional groups will provide a stronger interaction with an analyte having a similar functional group, enabling greater retention and resolving power. Therefore, the stationary phase preferably comprises functional groups that are like those present in the analytes to be separated. Consequently, non-polar stationary phases primarily separate analytes on the basis of boiling points (vapor pressure). Conversely, a polar stationary phase can be used to separate polar analytes.

Coating efficiency (i.e., how well the column or support is coated with the stationary phase) depends on the column type, coating method, and stationary phase material. In general, retention and sample capacity tend to increase with increasing stationary phase thickness, but at the cost of column efficiency (i.e., theoretical plate number). For wall-coated open columns, the stationary phase coating preferably comprises a relatively thin film of the stationary phase material uniformly coated on the inner wall of the column.

A thin, uniform coating enables a short and consistent residence time of the mobile phase analyte in the stationary phase, enabling sharp band definition and a narrow retention time distribution of the eluting analyte molecules. Therefore, thinner films can provide higher resolution for high-boiling point analytes. Thicker film columns are inherently more inert and can be used with more volatile analytes or for separations that are performed at lower column temperatures.

In addition, the stationary phase should be chemically stable and not react irreversibly with the mobile phase. Especially for temperature programming, the stationary phase material should have a wide operating temperature range and have a low vapor pressure at elevated column temperatures. In particular, the presence of residual volatiles and low-boiling point species in the stationary phase material can cause the column to bleed and contaminate the detector. Conditioning the column by purging the column at elevated temperature with a high-purity carrier gas prior to using the column for analyses can remove the residual volatiles and extend the column lifetime.

With fused-silica columns, the fused silica surface is pretreated prior to wall coating to deactivate the silanol surface sites and to create a surface that is more wettable by the stationary phase. The deactivated column is then coated with a uniform thin film (e.g., less than 8 µm thickness) of the stationary phase material on the inner wall of the clean, de-activated fused-silica tubing. Typical stationary phases used with fused-silica columns include polysilioxanes and polyethylene glycol phases. Polysiloxane phases can have high solute diffusivities and excellent chemical and thermal stability. Furthermore, polysiloxanes can have a variety of functional groups that exhibit a range of polarities. Polyethylene glycol phases typically have high selectivity for polar analytes. Depending on the material, stationary phases are typically prepared by solvent evaporation or solution-coating methods. The stationary phase can be further immobilized to provide greater chemical and thermal stability by in-situ crosslinking and/or chemical bonding to the fused-silica column. For example, the fused-silica column can be coated with an OH-terminated polysiloxane and heated to an elevated temperature to initiate condensation reactions between the hydroxyl terminations and the surface silanols of the fused silica to achieve a tightly bonded phase.

Recently, portable, handheld microanalytical systems, which have been termed "chemical laboratories on a chip," have been developed based on gas chromatography to enable the rapid and sensitive detection of particular chemicals, including pollutants, toxic industrial chemicals, high explosives, and chemical and biological warfare agents. Both open and packed in-chip channels have been used with current GC-based microanalytical systems. In particular, etched silicon channels are commonly used for microfabricated GC columns. Anisotropic wet etching or reactive ion etching can be used to form high-aspect-ratio rectangular channels with precisely controlled channel depth and width in a substrate. Typically, rectangular channels are about 10 to 100 microns wide and about 200 to 400 microns deep etched in the surface of a silicon wafer. For dense packing, the channels typically have a spiral or serpentine pattern in a die that is approximately one square centimeter in area. Overall column length is typically about 1 meter for open channels and as short as 10 centimeters for packed channels. Such high-aspect-ratio rectangular channels can provide relatively high column efficiency combined with relatively high volumetric flow rates and high stationary phase surface area. See C. M. Matzke et al., "Microfabricated Silicon Gas Chromatographic MicroChannels: Fabrication and Performance," *Proceedings of SPIE, Micromachining and Microfabrication Process Technology IV,* 3511, 262 (1998); and G. Lambertus et al., "Design, Fabrication, and Evaluation of Microfabricated Columns for Gas Chromatography," *Anal. Chem.* 76, 2629 (2004); which are incorporated herein by reference.

However, silicon-based microfabricated columns are expensive to process, require highly specialized flow interconnects, and have flow and separation limitations due to channel cross-section and length. Therefore, microfabricated columns manufactured from materials other than silica and glass, especially metals, are being developed. These alternate column materials can enable columns that are easier and less expensive to fabricate, can provide enhanced durability and strength, and yet can provide the chemical inertness of silicon.

Non-silicon columns can be fabricated out of virtually any material using a variety of micromachining techniques. For example, the GC column can be fabricated using a LIGA process (LIGA is the German acronym for Lithographie, Galvanoformung, and Abformung) as described in U.S. Pat. No. 6,068,684 to Overton, which is incorporated herein by reference. High-aspect-ratio channels can be easily formed in a wide variety of substrate materials using the LIGA-based techniques. Using a LIGA-based process to form a channel in a substrate, a thick layer of positive photoresist (e.g., PMMA) can be exposed to the x-ray beam through a patterning mask. The exposed areas of the photoresist can then be developed to provide a mold of the channel. If the mold is to be filled by electroforming, the photoresist mold can first be coated with a plating base. A structural material can then be electroformed on the plating base to fill the mold and form the walls of the channel. The rough, electroplated free surface of the filled mold can then be planarized by diamond lapping or the like. The remaining resist mold material can then be dissolved away to provide a hollow channel in the electroformed substrate. Typical LIGA-based column metals include copper and nickel. However, a wide variety of column materials can be deposited using LIGA processes, including gold, tantalum, chromium, aluminum, titanium, iron, metal alloys, and silicon.

Typically, the inside surfaces of the microfabricated channel is coated with a stationary phase material, such as a polymer, to enhance the separation of the chemical analytes of interest in the gas sample. However, the rectangular geometry is difficult to coat with a satisfactorily uniform stationary phase using conventional solvent evaporation or solution-coating methods. Sagging and pooling results in buildup of the stationary phase in the corners of the rectangular channel. This leads to a lower coating efficiency and tailing of the elution bands.

The evolution of portable, handheld microanalytical systems requires new stationary phase materials and coating methods that are compatible with new column materials and chromatography applications. In particular, these column materials require unique and specialized chemical functionalization to prepare and wet the column surface and to bond a uniform stationary phase to the column wall.

SUMMARY OF THE INVENTION

The present invention is directed to a gas chromatography column, comprising a column formed in a conductive or semiconductive column material; an organic layer bonded to inner wall of the column, wherein the organic layer is formed by the reduction of an onium salt on the column material surface; and a stationary phase material bonded to the organic layer. The onium salt preferably comprises a diazonium, iodonium, or sulfonium salt. The organic layer can be a functionalized phenyl layer. The column material preferably comprises carbon, metal, or silicon. The stationary phase material can be a polysiloxane or a polyethylene glycol. The column can comprise a channel microfabricated in a substrate using a LIGA-based process or other micromachining process.

The invention is further directed to a method for preparing a stationary phase on a gas chromatography column, comprising reducing an onium salt on the surface of the column material to provide a functionalized organic layer; and reacting a stationary phase material with the functionalized organic layer. The reducing step can further comprise biasing the surface at the open circuit potential to enable electrochemical reduction of the onium salt.

Non-silicon, especially metallic, microfabricated columns may be manufactured and processed at a fraction of the cost of silicon-based columns. When functionalized with the use of onium salt chemistry, the columns can be coated with a uniform stationary phase. In addition, the method can be used to phase-coat conventional capillary columns or silicon-based microfabricated columns.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

DETAILED DESCRIPTION OF THE INVENTION

The present invention is directed to the functionalization of a gas chromatographic column with a stationary phase material using onium salt chemistry. Preferably, the onium salt comprises a diazonium, iodonium, or sulfonium salt. Accordingly, the stationary phase can be chemically bonded to a variety of column surfaces, in addition to silicon-based surfaces. For example, microfabricated columns comprising metals can be fabricated using techniques well known in the art. As an example of the present invention, aryldiazonium salt chemistry is used to coat nickel columns with a polydimethylsiloxane (PDMS) stationary phase. Diazonium chemistry is well developed. PDMS is a widely used stationary phase material. Nickel is an attractive column material, since it is inexpensive, easily machinable, and the material of choice for LIGA-based columns. However, it will be apparent to those skilled in the art that other onium salts, stationary phases, and column materials can be used to practice the invention as taught herein.

Recent work has shown that diazonium molecules self assemble via an electron transfer mechanism on many conducting and semiconducting surfaces. The chemical reaction of the diazonium salt can occur at ambient temperature with select reaction times, or expedited with the use of heat, light, or electrical potential. As a result of the reaction between the surface and the diazonium salt, a covalent bond is formed resulting in a stable surface with appropriate anchor points that can aid crosslinking and bonding an adsorbent stationary phase to the surface. See Stewart et al., "Direct Covalent Grafting of Conjugated Molecules onto Si, GaAs, and Pd Surfaces from Aryldiazonium Salts," *J. Am. Chem. Soc.* 126, 27 (2004); J. Pinson and F. Podovorica, "Attachment of organic layers to conductive or semiconductor surfaces by the reduction of diazonium salts," *Chem. Soc. Rev.* 34, 429 (2005); and U.S. patent application Ser. No. 11/065,894 to Dirk et al.; which are incorporated herein by reference.

Figure 1:
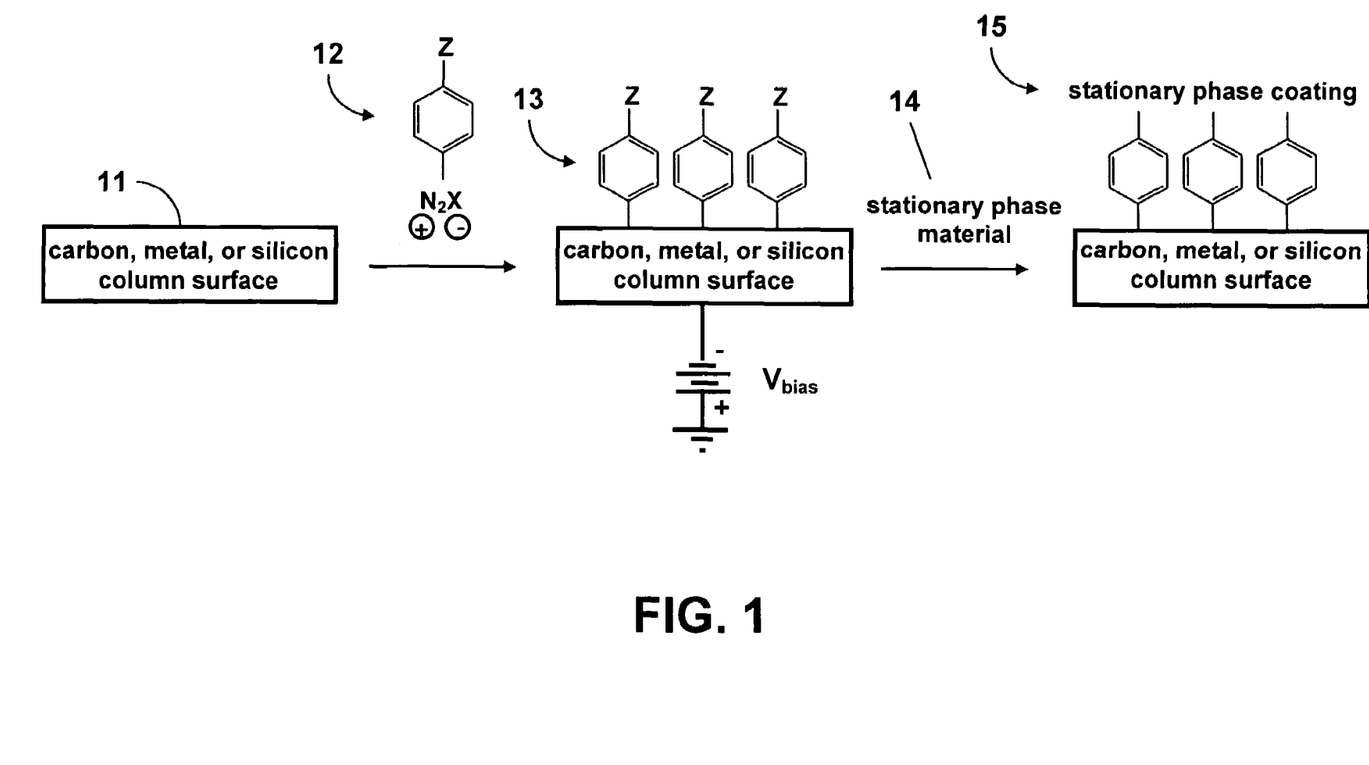
FIG. 1 shows a schematic illustration of a method to coat a column surface with a stationary phase using onium chemistry.

In FIG. 1 is shown a schematic illustration of an exemplary method of the present invention. The method comprises the reduction of an aryldiazonium salt 12 (e.g., $ZArN_2^+X^-$) on a carbon, metal, or silicon surface 11, resulting in the formation of an aromatic organic layer 13 bonded to the surface 11 that can be further functionalized with a stationary phase material 14. Prior to bonding, the surface 11 is prepared to be free of oxides or other inert passivating layers. The aryldiazonium salt 12 is dissolved in an anhydrous solvent (e.g., acetonitrile). An electron transfer from the surface reduces the diazonium salt and generates an aryl radical (not shown) upon loss of $N_2$. The aryl radical grafts to the exposed surface radical to form a covalently bound phenyl monolayer 13 that is chemically and thermally stable. In particular, the assembled monolayer 13 is resistant to aggressive reagents and many organic solvents. Spectroscopic analyses suggest that the bonded molecules adopt a close-packed, upright orientation (as shown) with the molecule backbone perpendicular to the substrate.

On many surfaces, the diazonium salts have been found to spontaneously self-assemble without an applied bias. Alternatively, the surface 11 can be biased (as shown) at the open circuit potential $V_{bias}$ to electrochemically reduce the aryldiazonium salt 12. If an external bias is used, a supporting electrolyte (e.g., tetrabutylammonium tetrafluoroborate) can be dissolved in the anhydrous solvent.

The functional groups Z of the assembled monolayer 13 can be reacted with other molecules to further modify the surface. Diazonium salts can be synthesized with a wide range of reactive functional groups Z, such as an alkyl, alkenyl, alkynyl, halogenoalkyl, carboxylic, ester, halide, nitro, alcohol, protected alcohol, amine, protected amine, thiol, or protected thiol, and more complex structures. In particular, the functional group Z can be reacted with a stationary phase material 14 (e.g., polysilioxane or polyethylene glycol) to bond a polymeric multilayer coating 15 to the surface 11. For example, the stationary phase material 14 can be terminated with a vinyl group ($CH_2=CH-$). The vinyl-terminated phase reacts with the diazonium-coated surface, providing polymer cross linkages and vinyl termination bonding. The thickness of the coating 15 can be controlled by the concentration of the stationary phase in the coating solution. In addition, the thickness of vinyl-terminated stationary phase materials can be controlled by chain transfer agents (e.g., thiols or chloroform). By preparing chromatographic columns with various stationary phase film thicknesses, the chemical separations can be designed relative to analyte physical and chemical properties (i.e., volatility and boiling point, polarity, and functionality). Numerous chemistries revolving around this basic reaction concept can permit tailoring the functionality of the surface to respective stationary phase chemistry, for example, phenyl-modification or hydroxyl termination. For example, hydroxyl-terminated stationary phases can be attached to the functionalized phenyl layer via condensation reactions.

Figure 2:
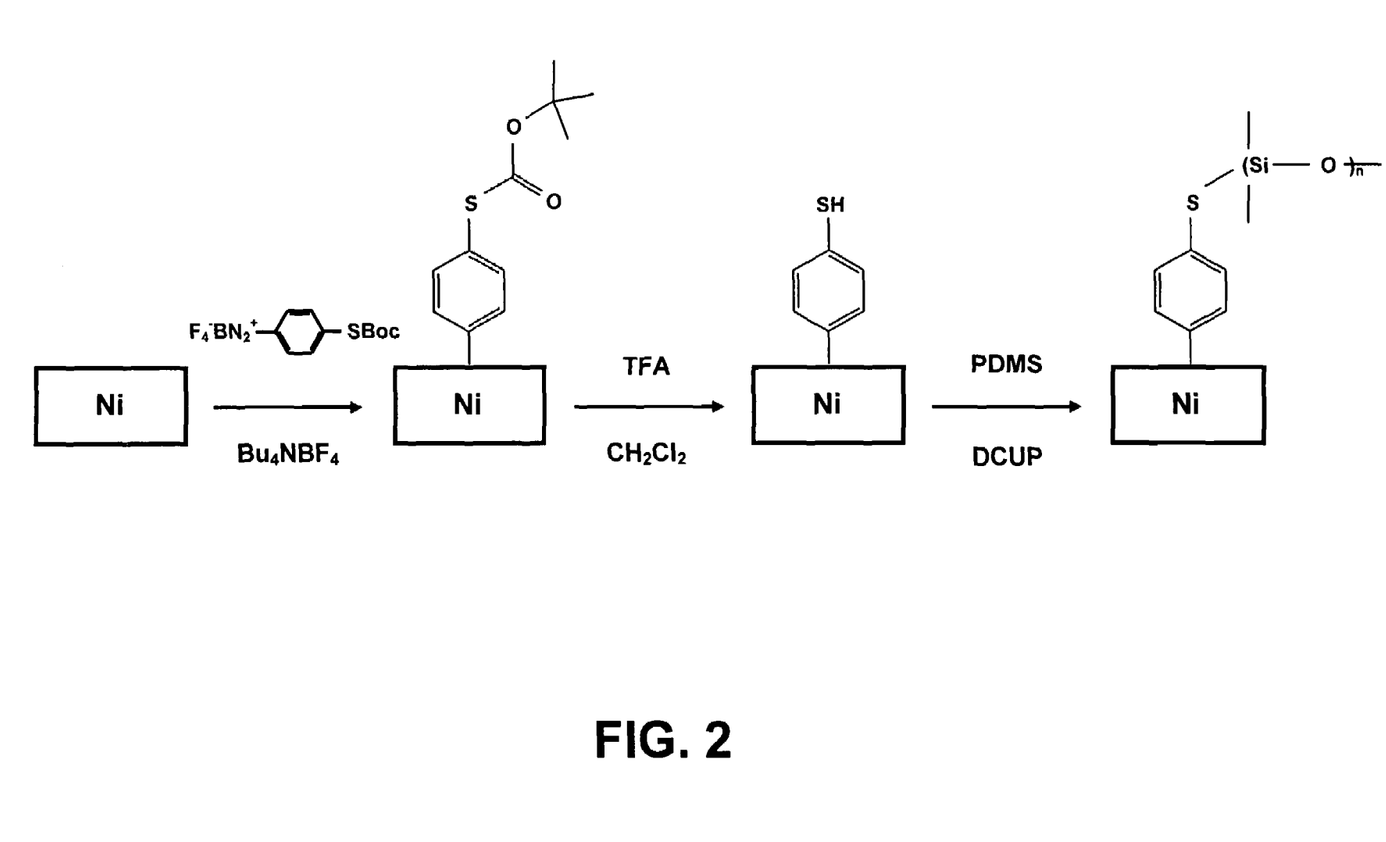
FIG. 2 shows a schematic illustration of a nickel column that was functionalized using aryldiazonium chemistry and bonded with a polydimethylsiloxane (PDMS) stationary phase.

In FIG. 2 is shown an example of the present invention, wherein a nickel column was functionalized using aryldiazonium chemistry and bonded with a polysiloxane stationary phase. The surface of a nickel capillary column (0.52 mm O.D.×0.20 mm I.D.×1 m long) was prepared by sequentially washing in methylene chloride, acetonitrile, and an ammonium hydroxide solution to remove the surface oxide and expose a fresh nickel surface. The nickel column was filled with a solution of 4-tert-butoxycarbonylsulfanylbenzenediazonium tetrafluoroborate (15 mg) dissolved into degassed acetonitrile (20 mL). A thiocarbonylbenzene monolayer was formed on the nickel surface after incubation with the diazonium salt for 30 min. After diazonium assembly, the column was rinsed in acetonitrile. The reactive thiol was then unmasked by filling the column with a solution of trifluoroacetic acid (TFA, 5 drops) dissolved in methylene chloride (20 mL) and allowing the solution to incubate for 10 min. After deprotection, the column was rinsed in methylene chloride. The thiol-functionalized column could then be coated with a polysiloxane stationary phase material. Vinylated PDMS (100 mg) was dissolved in methylene chloride (1 mL) and pentane (750 μL). To this solution was added a 5% (w/v) solution (250 μL) of dicumylperoxide (DCUP) in toluene. The column was filled with the reactive solution, attached via a manifold to a vacuum oven assembly, and reacted under inert gas to bond the PDMS phase. The column was conditioned by temperature ramping at 1° C./min and holding the reacted column at 200° C. for 2 hours.

Figure 3:
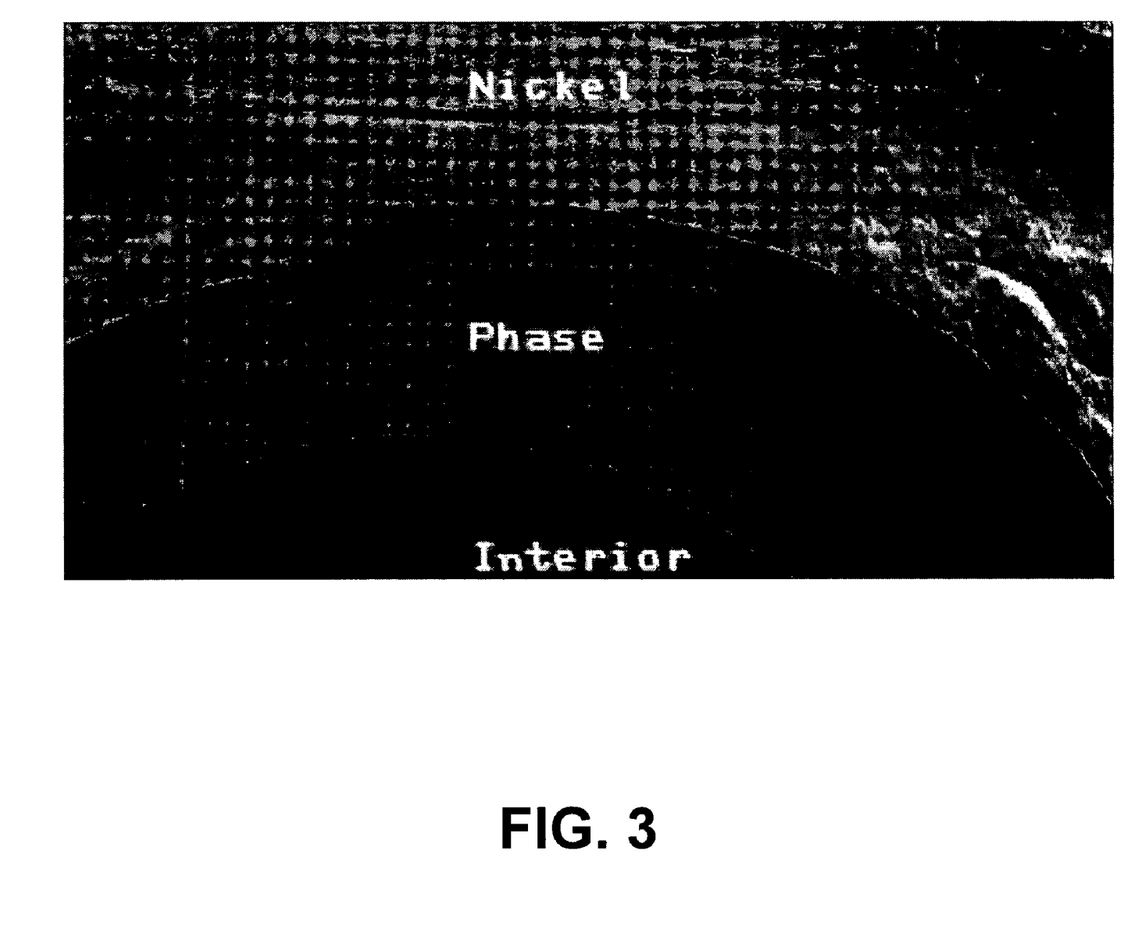
FIG. 3 shows a scanning electron micrograph (SEM) of a cross-section of a nickel capillary column coated with the PDMS stationary phase using aryldiazonium chemistry.

In FIG. 3 is shown a scanning electron micrograph (SEM) of a cross-section of the exemplary nickel column coated with the PDMS stationary phase according to the method described above. The SEM shows the effective bonding of the stationary phase to the nickel surface via the diazonium chemistry. The PDMS stationary phase is about 4 μm thick. The SEM indicates that very uniform thickness stationary phase coatings can be obtained using this method.

Figure 4:
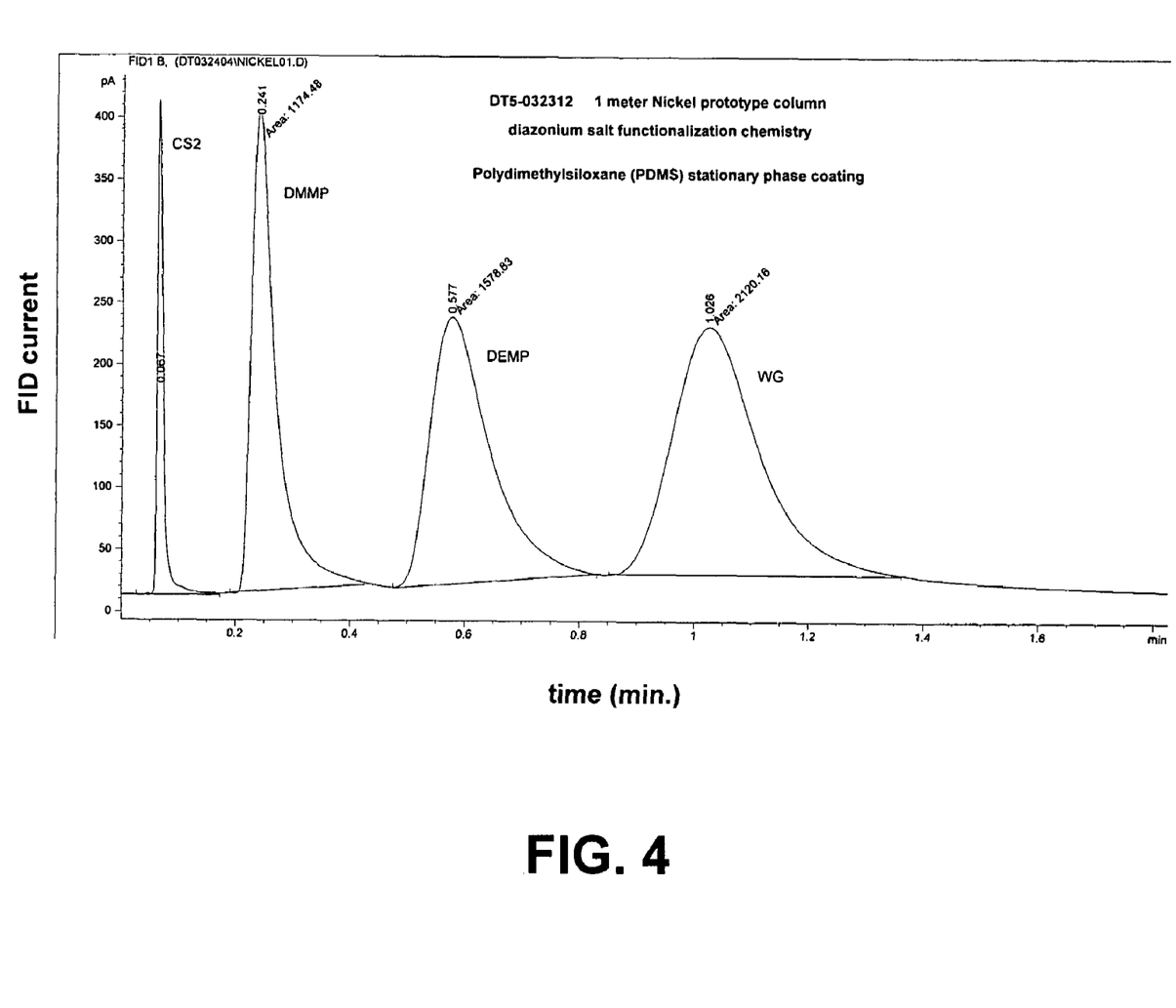
FIG. 4 shows a chromatogram of a mixture of polar analytes separated isothermally using a 1-meter-long nickel capillary column prepared with aryldiazonium chemistry and phase coated with PDMS.

In FIG. 4 is shown a chromatogram of a mixture of polar analytes, dimethyl methyl phosphonate (DMMP), diethyl methyl phosphonate (DEMP), and wintergreen (WG) dissolved in carbon disulfide (CS2), obtained using an isothermal 1-meter-long nickel capillary column prepared with aryldiazonium chemistry and phase coated with PDMS, as described above. The column was maintained at an operating temperature of 80° C. with a nitrogen carrier gas flow of 6 sccm. The separated analytes were detected with a conventional flame ionization detector (FID). The column temperature was kept at 80° C. Approximately Gaussian peak shapes, with little peak tailing, were obtained for the polar analytes, indicating conformal coverage of the column walls with the stationary phase. Good resolution is indicated by the baseline separation of the analytes. The chromatogram indicates that the rapid separation and resolution required for fast response-time portable gas analyzers can be achieved with this method.

Figure 5:
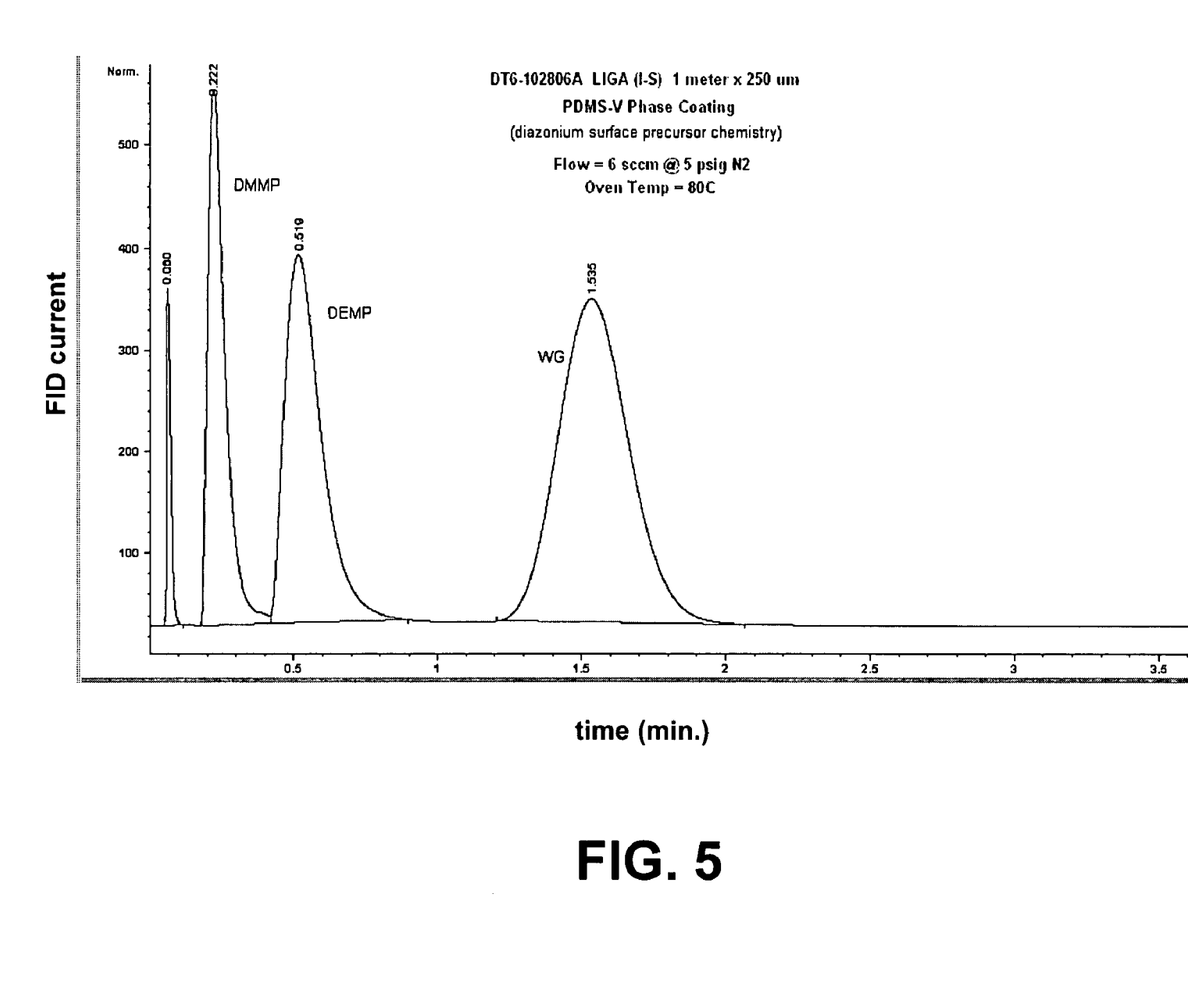
FIG. 5 shows a chromatogram of a mixture of polar analytes separated isothermally using a 1-meter-long nickel column fabricated using LIGA processes and prepared with aryldiazonium chemistry and phase coated with PDMS.
Figure 6:
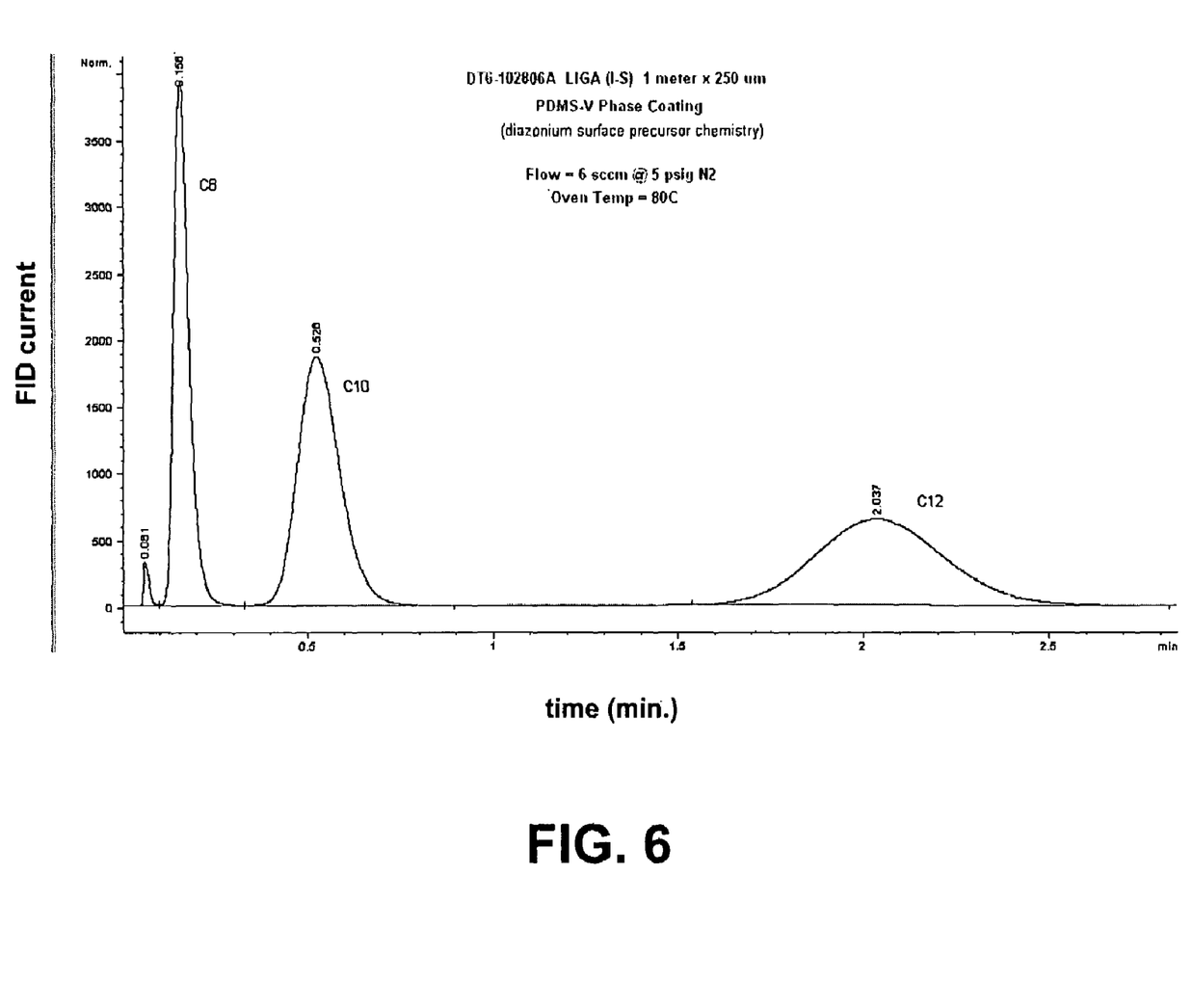
FIG. 6 shows a chromatogram of a mixture of nonpolar analytes separated isothermally using a 1-meter-long nickel column fabricated using LIGA processes and prepared with aryldiazonium chemistry and phase coated with PDMS.

In FIGS. 5 and 6 are shown chromatograms obtained using a 1-meter-long nickel column that was fabricated using a LIGA process. FIG. 5 shows a chromatogram obtained using the same mixture of polar analytes and the PDMS stationary phase. FIG. 6 shows a chromatogram obtained using the PDMS stationary phase with a nonpolar mixture of C8, C10, and C12 hydrocarbons. In both chromatograms, well-separated Gaussian peaks are obtained, again indicating conformal coverage of the LIGA-based column walls with the stationary phase.

The present invention has been described as a stationary phase based on onium salts. It will be understood that the above description is merely illustrative of the applications of the principles of the present invention, the scope of which is to be determined by the claims viewed in light of the specification. Other variants and modifications of the invention will be apparent to those of skill in the art.

We claim:

1. A gas chromatography column, comprising:
   a column formed in a conductive or semiconductive column material;
   an organic layer bonded to inner wall of the column, wherein the organic layer is formed by the reduction of an onium salt on the column material surface; and
   a stationary phase material bonded to the organic layer.

2. The gas chromatography column of claim 1, wherein the onium salt comprises diazonium salt, iodonium salt, or sulfonium salt.

3. The gas chromatography column of claim 2, wherein the diazonium salt comprises aryldiazonium salt.

4. The gas chromatography column of claim 1, wherein the organic layer comprises a functionalized phenyl layer.

5. The gas chromatography column of claim 1, wherein the onium salt comprises a reactive functional group.

6. The gas chromatography column of claim 5, wherein the reactive functional group comprises an alkyl, alkenyl, alkynyl, halogenoalkyl, carboxylic, ester, halide, nitro, alcohol, protected alcohol, amine, protected amine, thiol, or protected thiol.

7. The gas chromatography column of claim 1, wherein the stationary phase material comprises a polysiloxane or a polyethylene glycol.

8. The gas chromatography column of claim 1, wherein the column material comprises carbon, metal, or silicon.

9. The gas chromatography column of claim 8, wherein the metal comprises copper, nickel, gold, tantalum, chromium, aluminum, titanium, iron, or metal alloys.

10. The gas chromatography column of claim 1, wherein the column comprises a channel formed in a substrate using a micromachining process.

11. The gas chromatography column of claim 10, wherein the micromachining process comprises a LIGA-based process.

12. A method for preparing a stationary phase on a gas chromatography column, comprising:
    reducing an onium salt on the surface of the column material to provide a functionalized organic layer, and
    reacting a stationary phase material with the functionalized organic layer to provide a stationary phase bonded to the inner wall of the column.

13. The method of claim 12, wherein the reducing step further comprises applying a cathodic voltage bias to the surface to electrochemically reduce the onium salt.

14. The method of claim 13, wherein the surface is biased at the open circuit potential of the onium salt.

15. The method of claim 12, wherein the onium salt comprises diazonium salt, iodonium salt, or sulfonium salt.

16. The method of claim 15, wherein the diazonium salt comprises aryldiazonium salt.

17. The method of claim 12, wherein the functionalized organic layer comprises a functionalized phenyl layer.

18. The method of claim 12, wherein the functional group comprises an alkyl, alkenyl, alkynyl, halogenoalkyl, carboxylic, ester, halide, nitro, alcohol, protected alcohol, amine, protected amine, thiol, or protected thiol.

19. The method of claim 12, wherein the stationary phase material comprises a polysiloxane or a polyethylene glycol.

20. The method of claim 12, wherein the column comprises a channel formed in a substrate using a micromachining process.

21. The method of claim 20, wherein the micromachining process comprises a LIGA-based process.

* * * * *